United States Patent [19]

Wergeland et al.

[11] Patent Number: 5,008,197
[45] Date of Patent: Apr. 16, 1991

[54] PROCESS AND A DEVICE FOR IMPROVED OXYGENATION OF BIOLOGICAL CULTURES

[76] Inventors: Ivar Wergeland, Granitvägen 19B, S-75243 Uppsala; Ingeborg C. Senstad, Ornevn. 51, N-1340 Bekkestua, both of Norway; Eirik Nestaas, 70 High Rock Ter., Newton, Mass. 02167

[21] Appl. No.: 343,662

[22] Filed: Apr. 27, 1989

Related U.S. Application Data

[63] Continuation of Ser. No. 758,667, Jul. 9, 1985, abandoned.

[30] Foreign Application Priority Data

Nov. 10, 1983 [SE] Sweden ............................... 8306190

[51] Int. Cl.⁵ .......................... C12N 5/02; C12M 3/02
[52] U.S. Cl. .......................... 435/240.24; 435/240.25; 435/284; 435/286; 435/315; 435/818
[58] Field of Search ............... 435/284, 285, 286, 313, 435/315, 288, 299, 311, 240.1, 240.23, 240.24, 240.25, 240.46, 240.2, 818; 366/255, 273, 274; 261/104, 87

[56] References Cited

U.S. PATENT DOCUMENTS

| | | | |
|---|---|---|---|
| 3,900,186 | 8/1975 | Balas | 366/273 X |
| 4,596,779 | 6/1986 | Ono | 435/284 X |
| 4,649,114 | 3/1987 | Mittenburger et al. | 435/284 X |
| 4,649,118 | 3/1987 | Anderson | 435/284 X |

FOREIGN PATENT DOCUMENTS

0053869 6/1982 European Pat. Off. ............ 435/286

*Primary Examiner*—Robert A. Wax
*Assistant Examiner*—William H. Beisner
*Attorney, Agent, or Firm*—Bacon & Thomas

[57] ABSTRACT

The present invention provides an improved method and apparatus for cultivating mammalian cells. The invention relates to reaction vessels having a mechanical stirrer therein. The improvement comprises supplying oxygen to the culture media in the vessel through at least one oxygen-permeable membrane which is located on the stirrer so that the oxygen permeable membrane provides enhanced oxygen transfer across the membrane which is in contact with the culture media. The method and apparatus provides improved oxygen transfer across the membrane in comparison to other devices in which the oxygen permeable membrane is not located on the stirrer.

9 Claims, 3 Drawing Sheets

PROCESS AND A DEVICE FOR IMPROVED OXYGENATION OF BIOLOGICAL CULTURES

This application is continuation of application Ser. No. 758,667, filed Jul. 9, 1985 now abandoned.

FIELD OF TECHNOLOGY

The present invention relates to an improved process and apparatuses for supplying oxygen (oxygenation) to biological cultures, especially for cultivating tissue or mammalian cells. More specifically the invention is concerned with the oxygenation of biological cultures using so-called microcarrier techniques, wherein e.g. tissue cells or mammalian cells are grown on a solid surface in the form of small carrier beads.

BACKGROUND OF THE INVENTION

Despite the significant developments of recombinant DNA techniques, there is an increasing demand for biological products obtained by cultivation of mammalian cells. Such cells are used for physiological and biochemical cell studies, as well as for the production of various virus vaccines, hormones, biochemicals, interferons, monoclonal antibodies, plasminogen activators, and the like.

Many tissue cells require a solid surface for growth and proliferation (so-called anchorage-dependent cells). In production scale it has been common to cultivate such cells on the inside of rotating bottles. In order to achieve sufficient cell amounts several hundreds of such bottles are used in a batch. This production system is cumbersome and labour and material consuming, and a further drawback is that it in practice is impossible to monitor and control the process.

An improvement of the solid surface cultivation technique is the use of growth surfaces in the form of so-called "microcarriers", i.e. small (150-250 micron diameter) bead-shaped particles of porous or solid polymers such as cross-linked dextran. By using the microcarrier technique there is obtained an improved ratio between the surface area available for cell growth and the total volume of the culture. For example, in a one liter bottle 3 g of microcarrier particles can provide a surface area of about 18,000 $cm^2$, whereas the inside of the same bottle only provides a growth area of about 400-500 $cm^2$, which means an increase of the available surface area by a factor of about 40. The microcarrier technique is used commercially for the production of virus vaccines.

Although the problem of available surface area as a limiting factor seems to have been solved by the microcarrier technique, there are other factors limiting the scale-up of the mammalian cell cultures. Of these limiting factors the problem of oxygen transfer is considered to be the most critical one. Thus, the cells require a steady supply of oxygen, and a linear relationship between oxygen demand and cell concentration is typically observed. Because of the proteins of the growth medium, bubble aeration would lead to severe foaming, and oxygen is therefore commonly supplied by surface aeration.

Microcarrier cultures have to be stirred for keeping the microcarriers in suspension. The density of typical microcarriers is about 1.03. The cell wall of mammalian cells is much thinner than the cell wall of microorganisms, which means that tissue cells are more sensitive to shearing forces. The number of collisions between the microcarriers increases with increasing stirring intensity. Because of these factors the cell yield increases with decreasing stirring intensity, and the ideal stirring intensity (in this respect) is the one at which the microcarriers are just about kept in suspension. This requirement on a comparatively low stirring seems to be the main reason for the insufficient supply of oxygen to the culture in surface aeration.

It has been proposed (Fleischaker R. J. et al, Oxygen Demand and Supply in Cell Culture, European J. Upl. Microbiol. Biotechnol. 12 (1981), p. 193-197) to solve the problem of supplying sufficient amounts of oxygen to cell cultures by providing thin-walled silicone tubing at the bottom of the cell cultivation vessel. However, also this proposal has been found to be inadequate for large scale operation. For example, about 30 m of 2.5 cm silicone tubing would be required for oxygenating a 1000 l batch of HeLa cells.

A summary of the state of the art in mammalian cell culture and the problems encountered in the scaling-up thereof has been made by M W Glacken et al in Trends in Biotechnology, Vol. 1, No. 4, 1983, p. 102-108, "Mammalian cell culture: engineering, principles and scale-up", which is incorporated herein by reference.

OBJECTS OF THE INVENTION

One object of the invention is to provide for improved oxygenation of the culture medium in biological cultures involving mechanical agitation of the cultivation medium.

A further object of the invention is to provide a process and apparatuses for improved oxygenation of tissue or mammalian cell cultures in order to make large-scale operation possible.

Another object of the invention is to provide for increased oxygenation in combination with low agitation intensity in the cultivation of tissue or mammalian cells, especially in suspension cultures such as solid surface cultivation using microcarriers.

A still further object of the invention is to provide for increased cell density in the cultivation of tissue cells or mammalian cells.

A particular object of the invention is to provide an improved process and apparatuses for tissue or mammalian cell culture, in which the culture can be conveniently monitored and controlled.

A still further object of the invention is to provide an improved method and apparatuses of the above indicated type in which the sterilization problems are minimized.

The above and other objects of the invention will appear from the following description of the invention.

SUMMARY OF THE INVENTION

The present invention is based on the discovery that the supply of oxygen to a biological culture, especially a tissue cell or mammalian cell culture, which is agitated by means of a mechanical stirrer, can be improved considerably if the oxygenation is performed through one or more oxygen-permeable membranes carried by the very stirrer.

In one aspect the invention thus relates to a process for the oxygenation of biological, especially tissue or mammalian cell cultures, wherein the cultivation is carried out in a closed vessel and the culture is agitated by means of a mechanical stirrer, said process being characterized in that oxygen is supplied to the culture through at least one oxygen-permeable membrane carried by the mechanical stirrer.

In another aspect the invention relates to a mechanical stirrer for biological, especially tissue or mammalian cell cultures, which stirrer is characterized in that it comprises at least one oxygen-permeable membrane and means for supplying oxygen-containing gas to said oxygen-permeable membrane or membranes.

In a still further aspect the invention relates to a cultivation vessel for mammalian cell culture, which is characterized in that it is provided with at least one stirrer having means for passing oxygen through an oxygen-permeable membrane into the surrounding culture medium.

It is believed that the unexpectedly increased transfer of oxygen through the oxygen-permeable membrane, compared to the use of stationary membranes of the same material (compare FIGS. 7, 8 and 9 below), is caused by the fact that the liquid film on the outside of the membrane gets thinner when it is located on the moving stirrer. The findings according to the invention indicate that the greatest resistance to oxygen transfer is in the liquid film and not in the membrane itself. This is in contrast to what has been reported by Fleischaker et al, cited above. It is, however, to be understood that the invention is not intended to be restricted by this theoretical explanation.

Although the term "biological culture" and the like as used herein, primarily is intended to include any liquid culture medium for the growth and multiplication or proliferation of tissue cells or mammalian cells and requiring mechanical stirring, it is to be understood that said term may also include the use of other biological materials, the growth and multiplication of which involves similar oxygenation problems. The term "microcarrier" is intended to include any particulate material capable of serving as a carrier for said biological materials. The term "oxygen-permeable membrane" and the like is intended to include any comparatively thin membrane, through which oxygen can permeate selectively when an oxygen pressure differential is applied across the membrane, and which serves as a barrier for the liquid culture medium. The oxygen-permeable membrane should be substantially inert to the mammalian cell culture, and it should preferably be easy to sterilize. A preferred class of oxygen-permeable membranes are silicone-membranes having a suitable oxygen-permeability, e.g. in the range of 2–200 $\mu$mole $O_2$ per atm. $cm^2$. h, especially in the range 6–20 $\mu$mole $O_2$ per atm. $cm^2$. h. The term "mechanical stirrer" is intended to include any mechanical means capable of causing agitation of the cell culture medium, and the invention is not intended to be restricted to any specific design of the stirrer.

DESCRIPTION OF PREFERRED EMBODIMENTS

Figure 1:
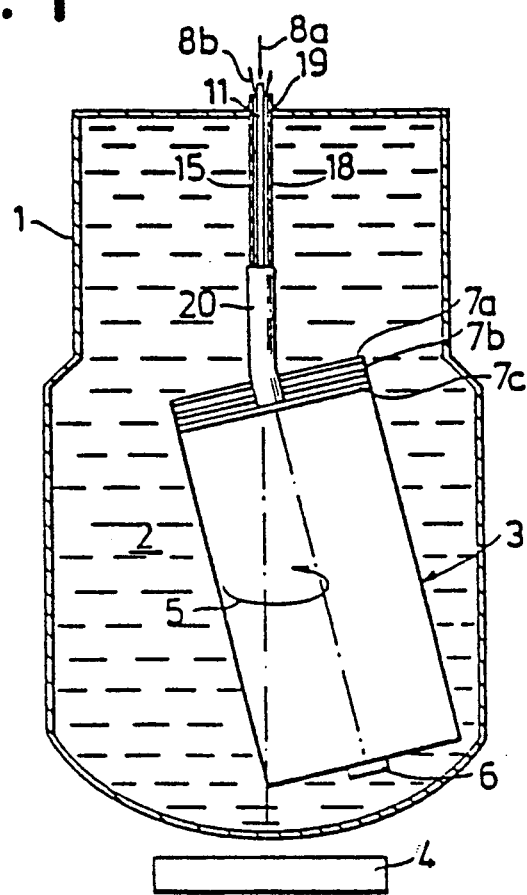
FIG. 1 is a schematic view illustrating the basic principle of the invention as applied to a special embodiment of the stirrer.

The invention will now be explained more in detail with reference to the enclosed drawings. It is, however, to be understood that the invention is not intended to be limited to the embodiments, which are shown in the drawings and described below, but it is intended to include any modification or variation thereof falling within the scope of the appended claims.

FIG. 1 shows a reactor vessel 1 which is filled with a liquid biological culture medium 2, such as a mammalian cell culture medium. In the preferred embodiment the liquid culture medium 2 contains suitable microcarrier beads which provide a solid surface for the cells to grow on. The microcarriers are kept suspended in the culture liquid by means of a stirrer 3, the agitation of which can be controlled by, for example, a device 4 capable of producing an adjustable magnetic field. The device 4, which is located outside the reaction vessel 1, causes the stirrer 3 to rotate along a path indicated by the arrow 5 by cooperation with permanent magnets 6 carried by the stirrer 3. The principle of magnetic stirring is well known to any person of average skill in the art. The agitation intensity of the stirrer 3 can be adjusted by variation of the magnitude of the magnetic field created by the device 4.

In the embodiment shown in FIGS. 1 to 6 the magnetic stirrer comprises three parallel support plates 7a, 7b and 7c, which are interconnected by supports 12 and 13, such as steele or glass tubes. The unit formed by the support plates 7a, 7b, 7c and the tubes 12, 13, has sufficient structural integrity to be able to perform the stirring function. In accordance with the invention the stirrer 3 is provided with at least one "gas pocket" made of oxygen-permeable material which is impervious to the surrounding liquid culture medium 2. Said gas pockets are connected to the exterior of the reaction vessel 1 for feeding oxygen-containing gas into the air pockets and discharging gas therefrom, as is illustrated by the arrows 8a and b respectively in FIG. 1. In the shown embodiment these air pockets are formed in that each of the support plates 7a, 7b and 7c is completely enclosed by an oxygen-permeable membrane 9a, 9b and 9c respectively. The gas pockets formed around each of the support plates 7a, 7b, 7c are preferably interconnected at the top or inlet portion by means of a common channel 10, which preferably also is formed of an oxygen-permeable material and is sealingly connected to a gas inlet conduit 11. At the bottom or outlet portion the gas pockets are connected to a second common channel 14, which is similar to the first common channel 10 and communicates with a gas outlet conduit 15. The channel 14 may to this end be connected to the conduit 15 via tubing 16, which may enter the support tube 13 and pass through a central bore 17 provided in the magnet 6, which is located in the support tube 13. As indicated by the arrows in FIGS. 2 and 3 the outlet gas may then flow freely inside support tube 13, to finally escape into outlet conduit 15 via suitable conduit means.

The support plates 7a, 7b, 7c are preferably made of a porous or mesh-type material such as steel mesh, so that the oxygen-containing gas can pass therethrough. The entire gas circulation system from the inlet conduit 11, through the feed channel 10, the air pockets inside membranes 9a, 9b, 9c, the discharge channels 14, 16, 17 and back to the exterior of the reaction vessel 1 through outlet conduit 15, is sealed from the liquid culture medium 2, which is thus prevented from entering into the gas circulation system. In accordance with the invention at least part of this gas circulation system consists of an oxygen-permeable membrane, so that oxygen can pass through the membrane and into the culture medium 2 during agitation. Since it is generally preferred to maximize surface area available for oxygen transfer, the major part of the walls are usually made of oxygen permeable membrane material, e.g. also the conduits 10, 11, 14, 15, 16, although certain parts may have to be of stronger non-permeable material to meet design, strength or other requirements.

It has to be emphasized that the shown embodiment of the stirrer is only one example of how the inventive concept can be put into practice, and it is believed that the efficiency of the oxygen transfer can be further increased by optimizing the design of the stirrer, also taking into consideration the nature of the specific culture for which it is to be used. For example, the support tubes 12, 13 could be replaced by suitable cross-bars or the like, which also interconnect the support plates 7a, 7b, 7c, but are spaced apart or provided with openings permitting the culture medium to also pass through the spaces between adjacent support plates, thereby further reducing the thickness of the liquid film on the outside of the membranes 9a, 9b, 9c and further increasing the oxygenation rate. It is also to be understood that the stirrer can have any other suitable number of stirring elements and/or any other suitable shape of the stirring elements than the shown plate shape. It is not either necessary to have the support members located inside the oxygen-permeable membranes (like the support plates 7a, 7b, 7c which are located inside the pocket membranes 9a, 9b and 9c respectively). For example, the required stirring rigidity can be obtained by enclosing a membrane pocket between a pair of wire netting, the openings of which permit the culture medium to contact the oxygen-permeable membrane. Such an embodiment can be advantageous when it is desired to operate at a comparatively high gas pressure inside the membrane pocket, the surrounding wire netting protecting the membrane pocket from excessive expansion.

Since e.g. mammalian cell cultures are extremely sensitive to contamination, it is essential that the inlets through the walls of the reaction vessel 1 are leak-tight. Since according to the invention the oxygen-containing gas is supplied to the stirrer itself, it is advantageous to locate the inlet and outlet conduits for the oxygen-containing gas inside the lead-through for the stirrer suspension means, as is the case in the embodiment shown in the drawings. Having only one inlet through the reactor wall reduces the risk of contamination of the culture. This risk has been reduced further in the shown embodiment, in which the suspension means for the stirrer 3 comprises a fixed (i.e. non-rotating) tube 18 such as a steele tube, which can be secured and sealed to the reactor wall by simple stationary sealing means 19. On the lower end of the preferably rigid inlet tube there is provided a flexible connecting tube 20, such as a strong silicone tube, which is sealingly connected to the gas discharge system, e.g. to the support tube 13. The flexible tube 20 also carries the stirrer 3, e.g. by being secured to extensions 12', 13' of the support tubes 12, 13. As can be seen from FIG. 1 not either the tube 20 rotates, but described a swinging motion illustrated by the arrow 5 in response to activation of the magnetic driving device 4.

It is to be understood that the invention is not either intended to be limited to any particular design of the lead-through or suspension or driving system for the stirrer. For example, also conventional rotary stirrers can be used, having rotary shafts passing through appropriately sealing bearings in the wall of the reaction vessel. Another alternative would be to replace the magnetic drive of the shown embodiment by a drive mechanism, which drives the tube 20 in a motion similar to that of the oar in a rowing boat, the inlet through the reactor wall serving as the "rowlock".

Figure 7:
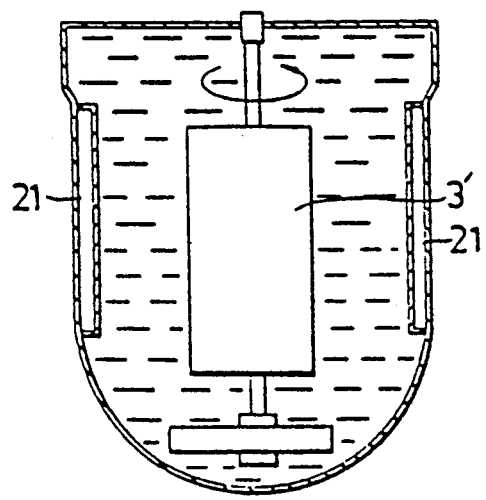
FIG. 7 is a schematic view illustrating, for comparative purposes, a prior art cultivation vessel having a stationary wall membrane.
Figure 2:
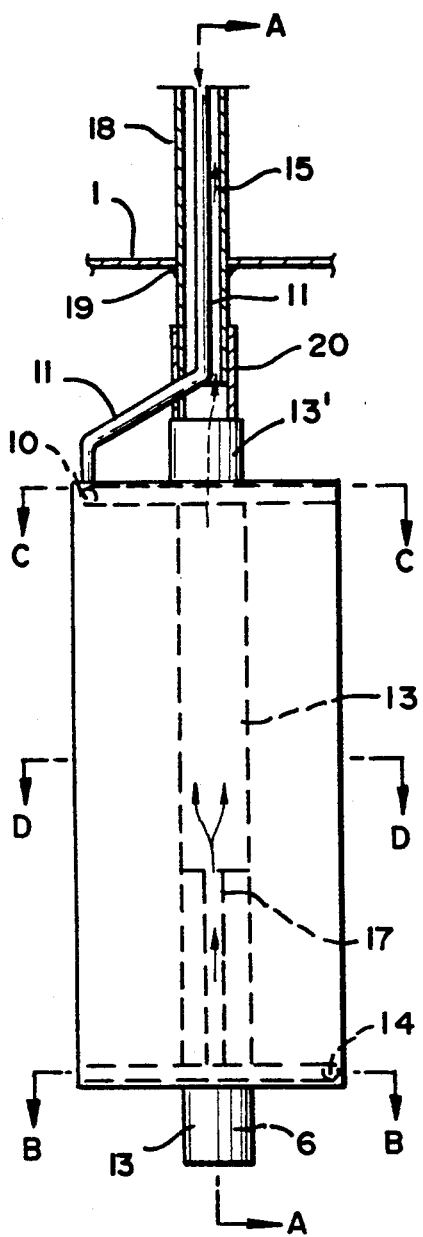
FIG. 2 is a schematic side elevational view, partly in section, of the embodiment of the stirrer according to FIG. 1.
Figure 3:
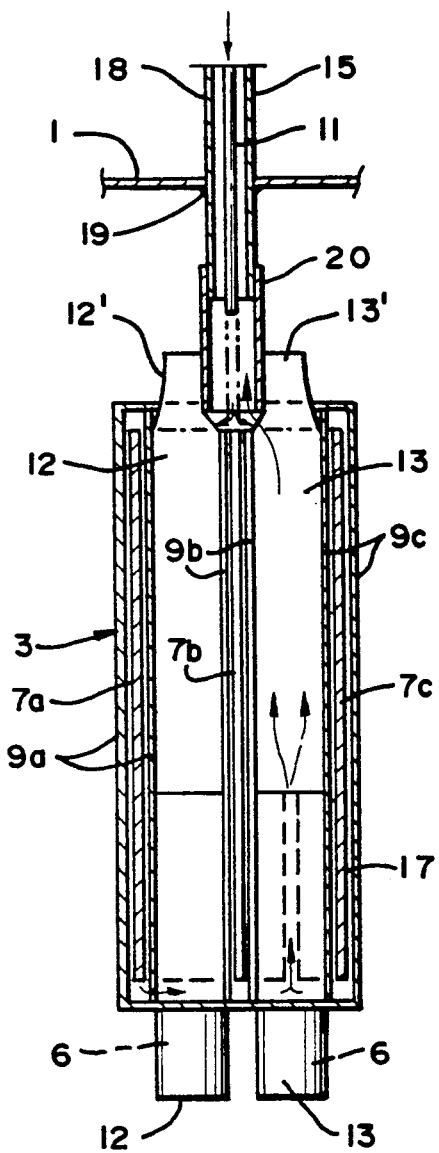
FIG. 3 is a schematic sectional view of the stirrer shown in FIG. 2, taken along A—A in FIG. 2.
Figure 4:
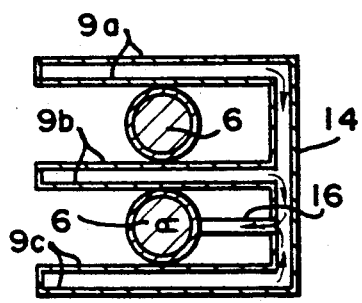
FIG. 4 is a schematic sectional view of the stirrer shown in FIG. 2, taken along B—B in FIG. 2.
Figure 5:
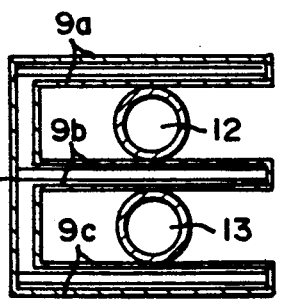
FIG. 5 is a schematic sectional view of the stirrer shown in FIG. 2, taken along C—C in FIG. 2.
Figure 6:
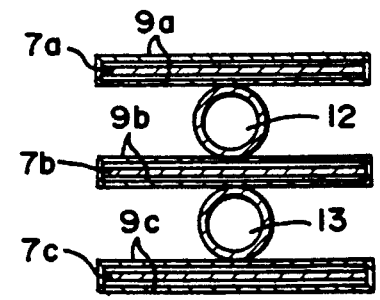
FIG. 6 is a schematic sectional view of the stirrer shown in FIG. 2, taken along D—D in FIG. 2.

In order to illustrate the considerably increased oxygen-transfer obtained by means of the invention the oxygen transfer coefficient was determined for (a) a reactor according to the invention as shown in FIG. 1, and (b) a reactor as shown in FIG. 7, having a conventional stirrer 3' and provided with a stationary oxygen-permeable gas pocket 21 (of the same silicone material as the membranes of the stirrer of FIG. 1) attached to the reactor wall.

Both reactors are operated completely filled with medium, and micro-carrier-bound cells are cultured semi-continuously with regular feeding/withdrawal of liquid, and under controlled pH and dissolved oxygen values. Oxygen uptake is measured dynamically (by shutting off air supply) as well as through an oxygen balance over the gas entering and leaving the reactors.

Figure 8:
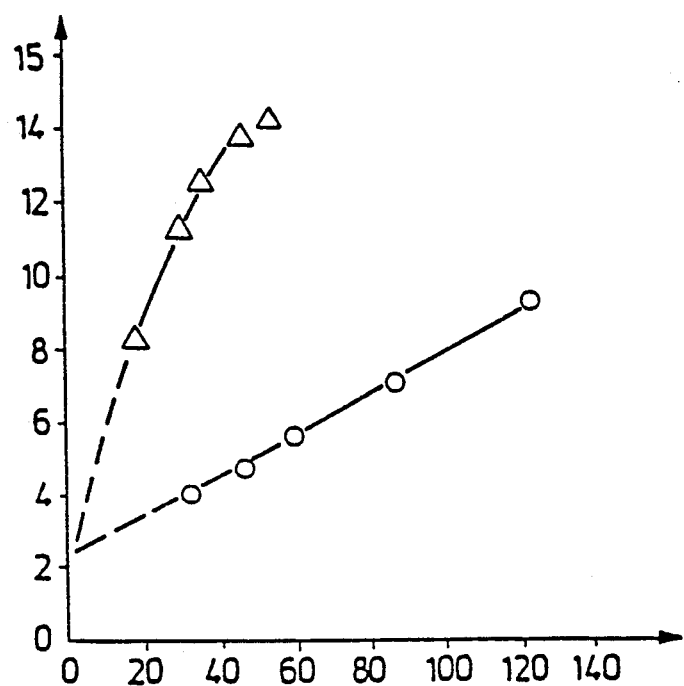
FIG. 8 is a diagram showing the correlation between oxygen transfer rate and agitation rate for the device according to the invention shown in FIG. 1, compared with the prior art device shown in FIG. 7.
Figure 9:
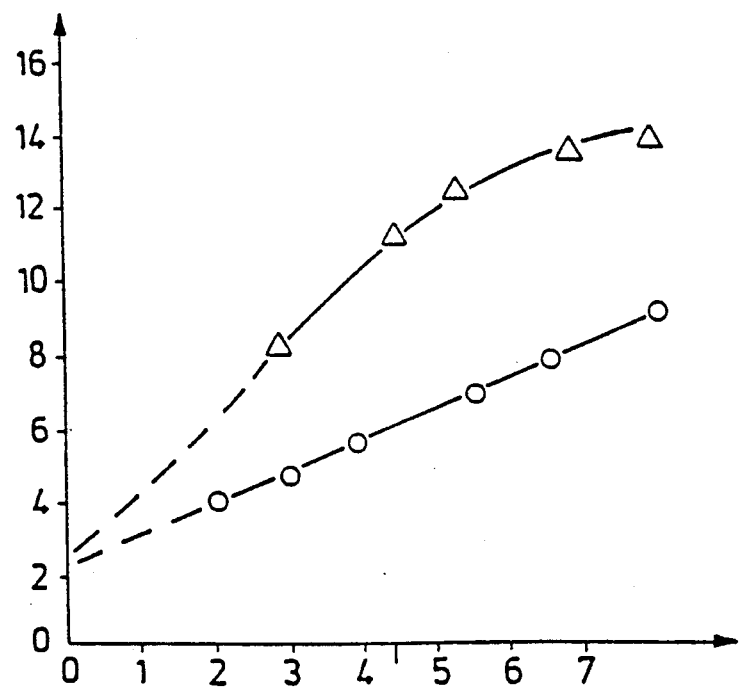
FIG. 9 is a diagram similar to that of FIG. 8 but based upon a theoretical model of average liquid shear rate instead of agitation rate.

In FIGS. 8 and 9 $\Delta$ represents the reactor of FIG. 1 and o represents the reactor of FIG. 7.

The test results appear from the diagram in FIG. 8, which shows that the reactor according to the invention (with the membrane on the stirrer) shows superior oxygen transfer, per membrane area ($\mu$mole $O_2/cm^2$-h-atm on the vertical axis), at any given agitation rate (rpm, horizontal axis). It can be noted that both reactors approach the same oxygen transfer value at zero agitation, as could be expected.

As the two reactors were not identical, the recorded values were recalculated as "integrated shear factor" (average liquid share rates). These data are presented in FIG. 9. It can be seen that the reactor according to the invention is still clearly superior to the comparison reactor having a stationary membrane (although the differences are less pronounced). It is, however, to be noted that the test reactor of the invention had some imperfections. For example, it can be seen from FIGS. 8 and 9 that the curve is not linear for the higher agitation and shear rates. This was caused by the fact that the stirrer turned from a circular to an elliptic path of movement at the higher agitation rates, but this was not considered in the calculations. It is most likely that the curves should in fact be linear. Since the reactor design was not either optimized (e.g. the support tubes largely inhibiting flow of culture liquid between adjacent membranes), it is expected that even higher oxygen transfer rates can be achieved.

EXAMPLE

The practical utility of the membrane-on-stirrer according to the invention was demonstrated by the following working example.
System: Vero cells cultivated on microcarriers (Cytodex ®1, available from Pharmacia Fine Chemicals AB, Uppsala, Sweden) in the standard medium E199.
Conditions:
Cell line: Vero (African Green Monkey, kidney)
Medium: E199 plus foetal calf serum 5%
Carrier: Cytodex ®1, 3 g per liter
Antibiotics: Penicillin 100 U per milliliter Streptomycin 100 μg per milliliter The fermentor was run for four weeks without any sign of contamination. Typically, the cell growth was doubled every 24–30 hours. When the microcarrier beads were almost covered with cells, 50 to 70% of the culture was withdrawn, medium with fresh (empty) microcarrier beads was added and the growth was continued.

Typical respiration was calculated to about $0.15 \times 10^{-12}$ mole $O_2$ per cell and hour.

Typical oxygen transfer was about $10-12 \times 10^{-6}$ mole $O_2$ per $cm^2$ of silicone membrane, hour and atmosphere (differential in partial $O_2$ pressure between the gas side and the culture side of the membrane).

At 50% oxygen saturation (0.1 atm. $O_2$) in the medium cell density was about $7-9 \times 10^5$ Vero cells per milliliter.

During this run the agitation was kept at 40 rpm. The agitation rate can, of course, be varied with regard to i.a. the specific design of the reactor and the stirrer, the specific culture and membrane used, and it is likely that the oxygen-transfer can be increased even further when optimizing a particular system.

In this test run the pressure differential was only 0.1 atm, but it can easily be increased to e.g. 0.6–0.9 atm or even higher, resulting in a cell density of about $6-8 \times 10^6$ cells per milliliter. This is about six times more Vero cells per milliliter than is obtained under normal conditions in presently available facilities.

It is finally to be mentioned that the invention makes it possible to calculate the difference in $O_2$ activity (atm) on the inlet and the outlet gas streams. In this manner the respiration can be calculated and related to cell density. This is much more convenient and more acurate than taking samples and counting the cells, which is the only method used in today's animal cell process industry.

The semipermeable membrane used in accordance with the invention not only transfers $O_2$ into culture medium, but is also capable of withdrawing $CO_2$ from a culture through the membrane. This is also an important factor, since a high $CO_2$ content would interfer with the buffer system of the culture, turning the pH to the acidic side at higher cell densitites. Similarly to $O_2$ it is also possible to conveniently measure $CO_2$ contents of the outlet gas from the system. Both the $O_2$ and $CO_2$ measurements can be used as a convenient tool for monitoring and controlling the cultivation process.

The supply of oxygen through a semipermeable membrane in accordance with the invention also eliminates the need for sterilization of the supplied oxygen-containing gas (whether it is air, only oxygen or any other oxygen-containing gas), since it is only the very atoms which pass through the membrane. This is normally a great problem in tissue culture, and gas sterilization equipment is complex and expensive.

We claim:

1. In a process for the oxygenation of biological cultures, comprising the steps of providing a liquid suspension of a biological culture in a closed reaction vessel and agitating said liquid suspension by means of a mechanical stirrer while supplying oxygen to said biological culture so as to promote the growth thereof, the improvement comprising supplying oxygen to said culture through at least one oxygen-permeable membrane carried by said stirrer, which is in direct contact with said liquid suspension.

2. A process according to claim 1, wherein said at least one membrane is a semi-permeable silicone membrane.

3. A process according to claim 1 or claim 2, wherein said biological culture is a tissue or mammalian cell culture.

4. A process according to claim 3, wherein said culture is grown on microcarriers suspended in said liquid culture medium.

5. A process according to claim 4, wherein said stirrer is substantially enclosed by said at least one membrane.

6. A process according to claim 3, wherein said stirrer comprises at least two agitation elements, each of which carries at least one oxygen-permeable membrane, said agitation elements being spaced apart so as to permit said liquid suspension to flow between adjacent ones of said agitation elements in contact with said membranes.

7. A process according to claim 4, wherein said stirrer comprises at least two agitation elements, each of which carries at least one oxygen-permeable membrane, said agitation elements being spaced apart so as to permit said liquid suspension to flow between adjacent ones of said agitation elements in contact with said membranes.

8. A reaction vessel for the cultivation of biological material requiring a supply of oxygen, comprising:
    (a) a closed reaction vessel for receiving a liquid suspension of said biological material to be cultivated,
    (b) a mechanical stirrer for agitating said liquid suspension,
    (c) means for sealingly suspending said stirrer in a wall portion of said closed vessel,
    (d) at least one oxygen-permeable membrane carried by said stirrer and forming at least one gas pocket, the outer side of which is in contact with said liquid suspension,
    (e) inlet conduit means for passing an oxygen-containing gas from the exterior of said vessel into said at least one gas pocket, and
    (f) separate outlet conduit means for discharging gas from said at least one air pocket to the exterior of said vessel.

9. A reaction vessel according to claim 8, wherein said inlet conduit means and said outlet conduit means pass through the wall of said reaction vessel within said suspension means for said stirrer.

* * * * *